United States Patent [19]

Koshar

[11] 4,429,093
[45] Jan. 31, 1984

[54] CYCLIC PERFLUOROALIPHATICDISULFONIMIDES AS POLYMERIZATION CATALYSTS

[75] Inventor: Robert J. Koshar, Mahtomedi, Minn.

[73] Assignee: Minnesota Mining and Manufacturing Co., St. Paul, Minn.

[21] Appl. No.: 472,956

[22] Filed: Mar. 7, 1983

Related U.S. Application Data

[62] Division of Ser. No. 229,870, Jan. 30, 1981, Pat. No. 4,387,222.

[51] Int. Cl.³ .................... C08F 4/00; C07C 143/44
[52] U.S. Cl. .................................. 526/205; 526/220; 526/225; 526/263; 526/332; 528/21; 528/23; 528/90; 528/408
[58] Field of Search .............. 548/123; 526/205, 220, 526/263, 332; 528/21, 23, 90, 408

[56] References Cited

U.S. PATENT DOCUMENTS 4,247,674  1/1981  Koshar et al. ................ 528/21

Primary Examiner—Joseph L. Schofer
Assistant Examiner—Peter F. Kulkosky
Attorney, Agent, or Firm—Donald M. Sell; James A. Smith; David R. Cleveland

[57] ABSTRACT

Acidic cyclic perfluoroaliphaticdisulfonimides, salts thereof, a process for making the same, curable compositions containing acidic cyclic perfluoroaliphaticdisulfonimides or salts thereof and cationically-sensitive monomers, and a process for using acidic cyclic perfluoroaliphaticdisulfonimides and salts thereof as catalysts for the cure of cationically-sensitive monomers.

5 Claims, No Drawings

CYCLIC PERFLUOROALIPHATICDISULFONIMIDES AS POLYMERIZATION CATALYSTS

This is a division of application Ser. No. 229,870 filed Jan. 30, 1981 now U.S. Pat. No. 4,387,222 issued June 7, 1983.

TECHNICAL FIELD

This invention relates to cyclic fluorocarbon acids, salts thereof, and a process for their synthesis. In another aspect, this invention relates to curable compositions containing cationically-sensitive monomers and said fluorocarbon acids or salts thereof. In yet another aspect, this invention relates to a process for curing cationically-sensitive monomers, such as epoxides, utilizing as catalyst said fluorocarbon acids or salts thereof.

BACKGROUND ART

Many types of useful linear fluorocarbon acids are known, such as trifluoromethanesulfonic acid, trifluoroacetic acid, and perfluoroalkanedisulfonimides of the formula $RSO_2NHSO_2R$, where R is a monovalent perfluoroalkyl group. German Pat. No. 22 39 817 discloses the preparation of perfluoroalkanedisulfonimides and their use as esterification catalysts, and U.S. Pat. No. 4,031,036 discloses the use of perfluoroaliphaticdisulfonimides as catalysts for the polymerization of cationically-sensitive monomers. In contrast to the linear fluorocarbon acids, few cyclic fluorocarbon acids are known. Henne et al., J.A.C.S. 73, 1103 (1951) have disclosed the cyclization of perfluorosuccinamide and perfluoroglutaramide to perfluorosuccinimide and perfluoroglutarimide, respectively.

The processes of formation of cyclic compounds by ring closure are generally known to be unpredictable because of ring instability, inability of functional groups to undergo ring closure, or decomposition of functional groups during the process of ring formation. For example, alkanedisulfonyl halides give linear olefinic sulfonamides on reaction with ammonia, e.g., 1,2-ethanedisulfonyl chloride yields $CH_2\!\!=\!\!CHSO_2NH_2$ on reaction with ammonia, see "The Organic Chemistry of Sulfur" by C. M. Suter, pp. 168-169, John Wiley and Sons, Inc., New York (1948).

DISCLOSURE OF INVENTION

The present invention provides, in one aspect, acidic cyclic perfluoroaliphaticdisulfonimides and their salts comprising compounds of the formula:

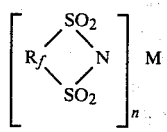

Formula I wherein $R_f$ is perfluoroalkylene having 2 to 4 backbone or catenary carbon atoms or perfluorocycloalkylene having 4 to 7, preferably 6, ring atoms, $R_f$ optionally being substituted by one or more, e.g., one to three, straight chain, branched, or cyclic perfluoroalkyl groups of 1 to 12, and preferably 1 to 4 carbon atoms, with $R_f$ having a total of up to 14 carbon atoms; M is a cation with a valence equal to n (e.g., hydrogen, ammonium, substituted ammonium, or a monovalent or polyvalent cation of a metal selected from the group consisting of Groups I-V and VIII, Subgroups VIB and VIIB, and the lanthanide and actinide series of the Periodic Table of the Elements); and n is an integer of 1 to 5. Preferably $R_f$ has the formula $-\!\!-\!\!CF_2\!\!-\!\!_m$ where m is 2 to 4.

The present invention also provides a process for the preparation of ring formation of said cyclic perfluoroaliphaticdisulfonimide ammonium salts, comprising the steps of adding ammonia to perfluoroaliphaticdisulfonyl fluoride precursor thereby forming the ammonium salt of cyclic perfluoroaliphaticdisulfonimide and ammonium fluoride, which ammonium salt can, if desired, be converted to acidic cyclic perfluoroaliphaticdisulfonimide, or to other salts of cyclic perfluoroaliphaticdisulfonimide.

The present invention also provides curable compositions comprising cationically-sensitive monomers and a catalytically effective amount of said acidic cyclic perfluoroaliphaticdisulfonimide or said salts thereof.

In yet another aspect, the present invention provides a process for the polymerization of cationically-sensitive monomers comprising the steps of:

(a) mixing with said monomers a catalytically effective amount of said acidic cyclic perfluoroaliphaticdisulfonimide or said salts thereof, thereby forming a mixture; and (b) allowing said mixture to polymerize, or heating said mixture to effect polymerization thereof.

DETAILED DESCRIPTION

In the practice of the present invention, said cyclic perfluoroaliphaticdisulfonimide ammonium salts can be prepared by cyclizing linear perfluoroaliphaticdisulfonyl fluoride precursor. Such ammonium salts can be further reacted to produce acidic cyclic perfluoroaliphaticdisulfonimides (i.e., compounds where M in Formula I is hydrogen and n is one). Other cyclic perfluoroaliphaticdisulfonimide salts of this invention are conveniently prepared by neutralization of said acidic cyclic perfluoroaliphaticdisulfonimide with substituted ammonium, metal hydroxide, oxide, carbonate, or acetate, or by other known salt formation reactions.

Precursor perfluoroaliphaticdisulfonyl fluorides have the formula $FSO_2R_fSO_2F$ and can be conveniently obtained by electrochemical fluorination of corresponding aliphaticdisulfonyl fluorides in accordance with the procedure described in U.S. Pat. No. 2,732,398. Corresponding cyclic perfluoroaliphaticdisulfonimide ammonium salts are conveniently prepared by the introduction of anhydrous gaseous ammonia into a solution of the precursor perfluoroaliphaticdisulfonyl fluoride in an inert solvent. Generally, about four moles of ammonia per mole of perfluoroaliphaticdisulfonyl fluoride is required to achieve good yields. Excess ammonia can be used if desired. The ammonia is passed into the perfluoroaliphaticdisulfonyl fluoride solution at a temperature sufficient to provide efficient and controllable reaction with the precursor perfluoroaliphaticdisulfonyl fluoride. Such temperature is preferably about $-25°$ to 100° C., and most preferably about 20° to 30° C. The addition of ammonia preferably occurs over a period of from about 1 to 10 hours. Suitable solvents are those that are essentially anhydrous and inert with respect to the reactants and include ethers such as diethyl ether and diisopropyl ether, hydrocarbons such as benzene, heptane, and cyclohexane, as well as halogenated hydrocarbons such as methylene chloride, ethylene chloride, and perfluorooctane. Diethyl ether is a preferred solvent. When diethyl ether is used as the solvent, the cyclization reaction proceeds with separation of insoluble ammonium fluoride from the diethyl ether solution of ammonium salt of the sulfonimide, thereby facilitating isolation of the desired product from ammonia fluoride by filtration.

The solvent of the filtrate or reaction mixture is removed, e.g., by evaporation or distillation, leaving ammonium perfluoroaliphaticdisulfonimide. Acidic cyclic perfluoroaliphaticdisulfonimides can be obtained from the ammonium salt of the cyclic perfluoroaliphaticdisulfonimide by distillation from a mixture of said ammonium salt and concentrated sulfuric acid (with excess sulfuric acid generally being used), or by ion-exchange of an aqueous solution of said ammonium salt using the acidic form of a cation exchange resin such as sulfonated polystyrene.

When the above order of addition is reversed, i.e., when perfluoroaliphaticdisulfonyl fluoride is added to liquid ammonia instead of addition of gaseous ammonia to perfluoroaliphaticdisulfonyl fluoride, then linear perfluoroaliphaticdisulfonamides (i.e., compounds bearing $-SO_2NH_2$ groups) rather than cyclic perfluoroaliphaticdisulfonimides are obtained in very high (e.g., 90 percent) yield. Cyclic perfluoroaliphaticdisulfonimides are not detectable products of such reaction.

The cyclic perfluoroaliphaticdisulfonimide substituted ammonium salts of this invention are formed by neutralization of the above-described acidic cyclic perfluoroaliphaticsulfonimides with a salt-forming primary, secondary or tertiary amine or a substituted ammonium hydroxide. Salt-forming amines include alkyl amines (such as methylamine, ethylamine, dimethylamine, diisopropylamine, trimethylamine, triisopropylamine, triisobutylamine, cyclohexylamine, ethylenediamine, and the like) heterocyclic amines (such as morpholine, pyridine, piperidine, and the like), guanidine, aminoguanidine, aromatic amines (such as aniline, and the like), and substituted ammonium hydroxides (such as tetramethylammonium hydroxide, tetraethylammonium hydroxide, benzyltrimethylammonium hydroxide, and the like).

The acidic cyclic perfluoroaliphaticdisulfonimides described above can be further reacted in standard salt formation reactions with derivatives (for example, oxides, carbonates, acetates, or hydroxides) of metals such as lithium, sodium, potassium, silver, magnesium, calcium, strontium, vanadium, manganese, cobalt, nickel, copper, zinc, cadmium, mercury, lead, tungsten, bismuth, lanthanum, and gadolinium to produce the corresponding metal salts of cyclic perfluoroaliphaticdisulfonimides of this invention. The cyclic perfluoroaliphaticdisulfonimide salts of metals of Groups III, IV, V and VIII, and Subgroups IB, IIB, VIB and VIIB of the Periodic Table of the Elements are preferred as catalysts for polymerization of cationically-sensitive monomers, e.g., epoxides. If desired, such metal salts can be formed without isolation of said acidic cyclic perfluoroaliphaticdisulfonimides by reaction of a suitable metal oxide or hydroxide with the cyclic perfluoroaliphaticdisulfonimide ammonium salt formed in the initial reaction of perfluoroaliphaticdisulfonyl fluoride with ammonia.

Examples of acidic cyclic perfluoroaliphaticdisulfonimides of this invention are cyclic 1,2-perfluoroethanedisulfonimide, cyclic 1,2-perfluoro(1-methylethane)disulfonimide, cyclic 1,3-perfluoropropanedisulfonimide, cyclic 1,3-perfluoro(1-methylpropane)disulfonimide, cyclic 1,3-perfluoro(2-butylpropane)disulfonimide, cyclic 1,3-perfluoro(2-decylpropane)disulfonimide, cyclic 1,3-perfluoro(1,2,3-trimethylpropane)disulfonimide, cyclic 1,4-perfluorobutanedisulfonimide, cyclic 1,4-perfluoro(1-methyl-2-ethylbutane)disulfonimide, and cyclic 1,2-perfluorocyclohexanedisulfonimide.

The acidic cyclic perfluoroaliphaticdisulfonimides of this invention and salts thereof (sometimes collectively referred to hereafter as cyclic perfluoroaliphaticdisulfonimides) are useful for the polymerization or curing of cationically-sensitive monomers. The term "monomers" as used herein includes not only low molecular weight cationically-sensitive materials, but also high molecular weight polymeric compositions, e.g., resins containing one or more cationically-sensitive polymerizable groups of the types described below, which in the presence of the cyclic perfluoroaliphaticdisulfonimides of this invention will undergo polymerization or crosslinking.

Said salts of the cyclic perfluoroaliphaticdisulfonimides of this invention are latent catalysts, particularly with respect to epoxides. The term "latent catalyst" as used herein means a catalyst which does not exhibit or manifest any substantial curing or catalytic effect on monomer admixed therewith during normal storage or handling of such mixtures until the mixture is subjected to heat for the purpose of activation, though some small or otherwise tolerable or insignificant curing of the monomer may take place before activation, as evidenced by a slight increase in viscosity. Similarly, a composition which has latency or is characterized as being latently curable is one which during the period prior to being heated to effect cure, exhibits little if any gelling, polymerization, etc., though some small or otherwise tolerable or insignificant curing may take place during such period.

The monomers that can be cured or polymerized with the cyclic perfluoroaliphaticdisulfonimides of this invention, using the latter in a catalytically effective amount, are those known to undergo cationic polymerization and include 1,2-, 1,3-, and 1,4-cyclic ethers (also designated as 1,2-, 1,3-, and 1-4-epoxides), vinyl ethers, N-vinyl compounds, ethylenically unsaturated hydrocarbons, cyclic formals, and cyclic organosiloxanes. As extensive list of cationically polymerizable monomers which can be used in this invention is given in U.S. Pat. Nos. 3,347,676 and 3,842,019.

The cyclic ethers which can be polymerized in accordance with this invention include those described in "Ring-Opening Polymerizations," Vol. 2, by Frisch and Reegan, Marcel Dekker, Inc. (1969). Suitable 1,2- cyclic ethers are the monomeric and polymeric types of epoxides. They can be aliphatic, cycloaliphatic, aromatic, or heterocyclic and will typically have an epoxy equivalency of from 1 to 6, preferably 1 to 3. Particularly useful are the aliphatic, cycloaliphatic, and glycidyl ether type 1,2- epoxides such as propylene oxide, epichlorohydrin, styrene oxide, vinylcyclohexane oxide, vinylcyclohexene dioxide, glycidol, butadiene oxide, glycidyl methacrylate, diglycidyl ether of bisphenol A, 3,4-epoxycyclohexylmethyl 3,4-epoxycyclohexanecarboxylate, 3,4-epoxy-6-methylcyclohexylmethyl 3,4-epoxy-6-methylcyclohexanecarboxylate, bis(3,4-epoxy-6-methylcyclohexylmethyl) adipate, dipentene oxide, epoxidized polybutadiene, 1,4-butanediol diglycidyl ether, polyglycidyl ether of phenolformaldehyde resole or novolak resin, resorcinol diglycidyl ether, and epoxy silicones, e.g., dimethylsiloxanes having cycloaliphatic epoxide or glycidyl ether groups. A wide variety of commercial epoxy resins is available and listed in "Handbook of Epoxy Resins" by Lee and Neville, McGraw-Hill Book Company, New York (1967) and in "Epoxy Resin Technology" by P.F. Bruins, John Wiley & Sons, New York (1968). Representative of the 1,3- and 1,4- cyclic ethers which can be polymerized in accordance with this invention are oxetane, 3,3-bis(-chloromethyl)oxetane, and tetrahydrofuran.

Another useful class of cationically-sensitive monomers which can be polymerized in accordance with this invention is represented by the general formula $CH_2=C(Y)XR$, where X is $-O-$ or $-NR'-$ (where R' is hydrogen or lower alkyl), R is hydrocarbyl, hydrocarbylcarbonyl, halohydrocarbyl, or hydroxyhydrocarbyl when X is oxygen, or R is hydrocarbyl, hydrocarbylcarbonyl, or hydrocarbylsulfonyl when X is nitrogen, and Y is hydrogen, alkyl, aryl, or other hydrocarbyl, or R (as hydrocarbylcarbonyl) and R' can be connected to form a 5- or 6-membered cyclic structure containing nitrogen as a hetero ring atom. The term "hydrocarbyl" is used herein in its usual sense to mean alkyl, alkenyl, aryl, cycloalkyl, cycloalkenyl, alkaryl, arylalkyl, and the like. In general, monomers of this type contain a vinyl group and are typified by vinyl alkyl ethers, such as vinyl methyl ether, vinyl ethyl ether, vinyl n-butyl ether, vinyl 2-chloroethyl ether, vinyl isobutyl ether, vinyl phenyl ether and vinyl 2-ethylhexyl ether, vinyl ethers of substituted aliphatic alcohols such as divinyl ether of butanediol, hydroxybutyl vinyl ether, and N-vinyl compounds such as N-vinyl-N-methyl octanesulfonamide and N-vinylpyrrolidone. A description of vinyl monomers and their use in preparing polymers is set forth in "Vinyl and Related Polymers", by Schildknecht, published by John Wiley & Sons, Inc., New York (1952).

Other cationically-sensitive monomers which can be polymerized in this invention include ethylenically unsaturated hydrocarbons such as isobutylene, 1,3-butadiene, isoprene, styrene, and divinylbenzene, especially the vinyl benzenes, cyclic formals such as trioxane, 1,3-dioxolane, 2-vinyl-1,3-dioxolane and methyl-1,3-dioxolane, and cyclic siloxanes which can contain various groups attached to the silicon atom such as a hydrocarbon radical (alkyl, aryl, alkaryl), an alkenyl hydrocarbon radical (vinyl, allyl or acryloyloxyalkyl), a halogenated hydrocarbon radical, a carboxy-containing hydrocarbon radical or ester group, a cyanohydrocarbon radical, hydrogen, halogen or a hydroxy group. Representative cyclic siloxanes are hexamethylcyclotrisiloxane, octamethylcyclotetrasiloxane, phenylheptamethylcyclotetrasiloxane, vinylheptamethylcyclotetrasiloxane, methacryloyloxymethylheptamethylcyclotetrasiloxane, bromomethylheptamethylcyclotetrasiloxane, 3-chloropropylheptamethylcyclotetrasiloxane, 1,2,3-tris(3,3,3-trifluoropropyl)-1,2,3-trimethylcyclotrisiloxane, acetoxymethylheptamethylcyclotetrasiloxane, cyanomethylheptamethylcyclotetrasiloxane, 1,2,3-trihydro-1,2,3-trimethylcyclotrisiloxane, and chloroheptamethylcyclotetrasiloxane. Other known cyclic siloxanes are listed in "Chemistry and Technology of Silicones" by Walter Noll, Academic Press, New York (1968), Tables 41, 44 and 45.

The cyclic siloxanes can also be polymerized in the presence of relatively low molecular weight linear siloxanes such as hexamethyldisiloxane, chloropentamethyldisiloxane and octamethyltrisiloxane which serve to terminate the growing chain and provide stable fluids or fluids having reactive end groups.

There is a host of commercially available cationically-sensitive monomers which can be used in this invention. In particular, cyclic ethers which are readily available include propylene oxide, oxetane, epichlorohydrin, tetrahydrofuran, styrene oxide, vinylcyclohexene oxide, glycidol, glycidyl methacrylate, octylene oxide, phenyl glycidyl ether, 1,2-butane oxide, diglycidyl ether of bisphenol A (e.g., "Epon 828" and "DER 331"), vinylcyclohexene dioxide (e.g., "ERL-4206"), 3,4-epoxycyclohexylmethyl-3,4-epoxycyclohexanecarboxylate (e.g., "ERL-4221"), 3,4-epoxy-6-methylcyclohexylmethyl-3,4-epoxy-6-methylcyclohexanecarboxylate (e.g., "ERL-4201"), bis(3,4-epoxy-6-methylcyclohexylmethyl)adipate (e.g., "ERL-4289"), aliphatic epoxy modified with polypropylene glycol (e.g., "ERL-4050" and "ERL-4052"), dipentene dioxide (e.g., "ERL-4269"), epoxidized polybutadiene (e.g., "Oxiron 2001"), silicone epoxy (e.g., "Syl-Kem 90"), 1,4-butanediol diglycidyl ether (e.g., "Araldite RD-2"), polyglycidyl ether of phenolformaldehyde novolak (e.g., "DEN-431," "Epi-Rez 521" and "DEN-438"), resorcinol diglycidyl ether (e.g., "Kopoxite"), polyglycol diepoxide (e.g., "DER 736"), polyacrylate epoxide (e.g., "Epocryl U-14"), urethane modified epoxide (e.g., "QX3599"), polyfunctional flexible epoxides (e.g., "Flexibilizer 151"), and mixtures thereof as well as mixtures thereof with co-curatives, curing agents, or hardeners which also are well known (see Lee and Neville and Bruins, supra). Representative of the co-curatives or hardeners which can be used are acid anhydrides such as nadic methyl anhydride, cyclopentanetetracarboxylic dianhydride, pyromellitic anhydride, cis-1,2-cyclohexanedicarboxylic anhydride, and mixtures thereof.

In general, the polymerization of cationically-sensitive monomers with the acidic cyclic perfluoroaliphaticdisulfonimides of this invention can be carried out at room temperature for the majority of cationically-sensitive monomers, although low temperature (e.g., $-10°$ C.) or elevated temperatures (e.g., 30° to 200° C., preferably 50° to 100° C.), can be used to either subdue the exotherm of polymerization or to accelerate the polymerization. In the case of latent salt catalysts of this invention, temperatures generally in the range of 50° to 250° C., preferably from 80° to 150° C., can be used. The temperature of polymerization and amount of catalyst will vary and be dependent on the particular cationically-sensitive monomer used and the desired application of the polymerized or cured product.

The amount of cyclic perfluoroaliphaticdisulfonimide to be used as a catalyst in this invention (i.e., a catalytically effective amount) should be sufficient to effect polymerization of the cationically-sensitive monomer under the desired use conditions. Such amount generally will be in the range of about 0.01 to 20 weight percent, perferably 0.5 to 5 weight percent, and most preferably 1 to 2 weight percent, based on the weight of cationically-sensitive monomer.

Solvents can be used to assist in dissolution of said cyclic perfluoroaliphaticdisulfonimide in the cationically-sensitive monomer. Representative solvents include acetone, methylene chloride, ethyl acetate, methyl ethyl ketone, acetonitrile, p-dioxane, and the dimethyl ether of ethylene glycol (glyme). In general, in compositions containing acidic cyclic perfluoroaliphaticdisulfonimide catalysts, basic solvents or basic impurities in the monomer are avoided to prevent deactivation of the acidic catalyst.

The curable or polymerizable compositions of this invention, consisting of or consisting essentially of the cationically-sensitive monomer(s) and said cyclic perfluoroaliphaticdisulfonimide as catalyst, can be used for applications like those cationically-sensitive monomer systems cured with other catalysts, such as epoxides cured with $BF_3$ or the complex of $BF_3$ with diethyl ether. Also, curable compositions of the invention comprising cationically-sensitive monomer(s), said cyclic perfluoroaliphaticdisulfonimide as catalyst, and other adjuvants (e.g., fillers, reinforcements, pigments, extenders, plasticizers and surface modifying agents) can be prepared in the same manner as compositions containing cationically-sensitive monomers, other catalysts, and adjuvants. For example, the curable compositions of this invention can be used as adhesives caulking and sealing compounds, casting and molding compounds, potting and encapsulating compounds, impregnating and coating compounds, etc., depending on the particular monomers and/or catalyst used. Where the catalyst is used in its latent form, the curable composition can be used as a one-component or cured-in-place system, such capability enhancing its use for the applications mentioned above. One particular application where such capability can be employed is in the electrical arts, where such latently curable compositions can be used to coat or impregnate for insulation or protective purposes electrical motor windings or coils, transformers, capacitors, electrical terminals, cables, and other electrical devices.

The curable epoxy composition of this invention can be used to make shaped articles of self-supporting, structural, filled or reinforced epoxy resin composites, such as glass fiber cloth reinforced epoxy resin composites, useful, for example, as repair materials. The various fillers, reinforcements, and other particulate materials to be mixed or coated with or dispersed in the curable compositions of this invention to make the composites of this invention, as well as methods of processing these materials in making the composites, and their applications, are those known to the art. In this connection, reference is made to "Modern Composite Materials," edited by Brautman and Krock, published by Addison-Wesley Publishing Company, Reading, Mass. (1967); and "Handbook of Fiberglass and Advanced Plastics Composites," edited by G. Lubin, published by Van Nostrand Reinhold Company, New York, N.Y. (1969).

The objects and advantages of this invention are further illustrated by the following examples, but the particular materials and amounts thereof recited in these examples as well as other conditions and details should not be construed to unduly limit this invention.

EXAMPLE 1

This example shows a general procedure useful for the preparation of acidic cyclic perfluoroaliphaticdisulfonimides of this invention.

Anhydrous ammonia (7 g) was bubbled into a solution of 21 g of 1,3-perfluoropropanedisulfonyl fluoride in 120 ml of anhydrous diethyl ether over a period of 4 hours. The mixture was filtered to remove ammonium fluoride and the filtrate evaporated giving 20.4 g of the ammonium salt of the cyclic perfluoroaliphaticdisulfonimide. A portion of such salt (10 g) was mixed with 20 ml of concentrated sulfuric acid. Distillation gave 7.7 g of cyclic 1,3-perfluoropropanedisulfonimide, b.p. 84°-85° C. at 5 mm Hg, and having the structure:

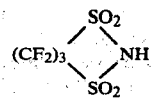

The identity of the compound was established by infrared, nuclear magnetic resonance, mass spectral and elemental analyses. The anhydrous compound is a solid at room temperature and forms a hydrate when exposed to atmospheric moisture.

EXAMPLE 2

Using the method of Example 1, cyclic 1,4-perfluorobutanedisulfonimide (b.p. 97°-98° C. at 5 mm Hg) was obtained in 60% yield from 1,4-perfluorobutanedisulfonyl fluoride.

EXAMPLE 3

Using the method of Example 1, cyclic 1,2-perfluoroethanedisulfonimide (b.p. 81°-82° C. at 5 mm Hg) was obtained in 63% yield from 1,2-perfluoroethanedisulfonyl fluoride.

EXAMPLE 4

This example shows the preparation of a cyclic perfluoroaliphaticdisulfonimide having a $CF_3$-substituted perfluoroalkylene moiety.

Using the method of Example 1, 20 g of 1,4-perfluorobutanedisulfonyl fluoride containing 7 mol % of 1,3-perfluoro(1-methylpropane)-disulfonyl fluoride was reacted with about 9 g of anhydrous ammonia, giving 16.6 g of mixed ammonium salts of cyclic 1,3-perfluoro(1-methylpropane)disulfonimide and cyclic 1,4-perfluorobutanedisulfonimide. The ammonium salts (7.4 g) were mixed with 25 ml of concentrated sulfuric acid. Distillation gave 3.8 g of a mixture of cyclic perfluoroaliphaticdisulfonimides, bp, 88°-90° C. at 4 mm Hg, containing about 10 mol % of cyclic 1,3-perfluoro(1-methylpropane)disulfonimide having the structure:

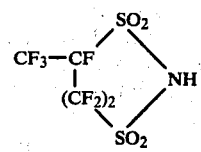

and 90 mol % of cyclic 1,4-perfluorobutanedisulfonimide.

EXAMPLE 5

This example illustrates the preparation of salts of cyclic perfluoroaliphaticdisulfonimides.

To a stirred mixture of 1.0 g of cyclic 1,4-perfluorobutanedisulfonimide and 5 ml of diethyl ether was added about 0.5 ml of diethylamine. The diethyl ether was allowed to evaporate and the residue azeotropically dried with toluene under reduced pressure. There was obtained 1.0 g after drying under vacuum of the diethylamine salt of cyclic 1,4-perfluorobutanedisulfonimide (m.p. 129°-131° C.).

A silver salt was prepared by neutralization of a stirred methyl alcohol solution of cyclic 1,3-perfluoropropanedisulfonimide with silver carbonate. The mixture was filtered to remove any excess carbonate and the filtrate evaporated under reduced pressure and finally under vacuum giving the silver salt of cyclic 1,3-perfluoropropanedisulfonimide which was a white solid.

The following examples show the catalytic properties of cyclic perfluoroaliphaticdisulfonimides of this invention.

EXAMPLE 6

A solution of 0.04 g of cyclic 1,2-perfluoroethanedisulfonimide and 0.14 g of essentially anhydrous acetone was prepared. Addition of about 0.04 g of such catalyst solution to one gram of divinyl ether of butanediol caused an immediate exothermic polymerization to a dark solid polymer.

EXAMPLE 7

Addition of about 0.1 g of the catalyst solution of Example 6 to 3.2 g of N-vinyl-2-pyrrolidinone caused an exothermic polymerization. After one hour at room temperature, a light orange, very viscous grease was obtained.

EXAMPLE 8

To 1.0 g of "ERL-4221" epoxide (commercially available from Union Carbide Co.) was added with stirring 0.05 g of cyclic 1,4-perfluorobutanedisulfonimide dissolved in 0.3 g of methylene chloride. Immediate gelation occurred, and after 15 hours at room temperature a clear, hard, brittle polymer was obtained. The cured polymer is suitable for use as a protective coating.

EXAMPLE 9

The diethylamine salt of cyclic 1,4-perfluorobutanedisulfonimide (0.03 g) and 3.0 g of "ERL-4221" epoxide were mixed at room temperature in an aluminum dish. The homogeneous composition remained fluid (no polymerization) for 20 hours but heating at 150° C. for 10 minutes provided a hard, brittle polymer suitable for use as a potting compound.

EXAMPLE 10

Using the method of Example 9, a mixture of 0.05 g of the silver salt of cyclic 1,3-perfluoropropanedisulfonimide and 2.5 g of "ERL-4221" epoxide was prepared. After storage at room temperature for 20 hours the mixture became a homogeneous clear fluid, indicating that the salt had dissolved. No evidence of polymerization was detected. Heating of the sample at 130° C. for 10 minutes gave a hard, brittle polymer.

EXAMPLE 11

To a dry glass vial containing 0.07 g of cyclic 1,3-perfluoropropanedisulfonimide was added 4.3 g of anhydrous tetrahydrofuran. The vial was flushed with nitrogen and capped. After storage at room temperature for 20 hours, a very viscous, transparent oil was obtained. A portion (1.3 g) of the oil was allowed to evaporate under vacuum giving 0.6 g of high molecular weight polytetrahydrofuran which was a white gum essentially insoluble in water. Soaking of the gum in water for one hour gave a non-tacky, tough gum.

EXAMPLE 12

A solution of 0.04 g of cyclic 1,3-perfluoropropanedisulfonimide and 0.24 g of ethyl acetate was added to 4.1 g of styrene. A very exothermic polymerization occurred. After one hour at room temperature a very viscous, light yellow grease was obtained.

EXAMPLE 13

To 0.02 g of cyclic 1,3-perfluoropropanedisulfonimide in a dry glass vial under nitrogen was added 2.5 g of octamethylcyclotetrasiloxane. The vial was capped and the contents stirred, using magnetic stirrer, at room temperature for two hours. A colorless polydimethylsiloxane gum having the flow characteristics of a very high molecular weight polymer was obtained. After storage at room temperature for 15 hours, a non-tacky gum was obtained.

EXAMPLE 14

Using the method of Example 13, cyclic 1,3-perfluoropropanedisulfonimide was combined in separate experiments with bromomethylheptamethylcyclotetrasiloxane and methacryloyloxymethylheptamethylcyclotetrasiloxane, to form mixtures containing 2 weight percent cyclic 1,3-perfluoropropanedisulfonimide. In each case, a clear, high molecular weight polysiloxane gum was obtained after the mixture was allowed to stand at room temperature for about 20 hours.

EXAMPLE 15

An ethyl acetate solution containing 25% by weight of a trimethylsilyl-terminated epoxy polysiloxane fluid having about 45 dimethylsiloxane units and four methyl[2-(3,4-epoxycyclohexyl)ethyl]siloxane units per molecule was prepared. To this solution was added the ammonium salt of cyclic 1,4-perfluorobutanedisulfonimide (2% by weight based on epoxy siloxane). The resulting mixture showed no evidence of gelation or change in viscosity after three days at room temperature. The mixture was coated on polyester film and the film heated at 90° C. for one minute giving a tack-free polymer coating.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. Curable compositions, comprising cationically-sensitive monomers and a catalytically effective amount of acidic cyclic perfluoroaliphaticdisulfonimides or their salts comprising compounds of the formula:

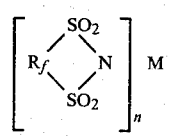

wherein $R_f$ is perfluoroalkylene having 2 to 4 catenary carbon atoms or perfluorocycloalkylene having 4 to 7 ring atoms, $R_f$ optionally being substituted by one or more straight chain, branched, or cyclic perfluoroalkyl groups of 1 to 12 carbon atoms, with $R_f$ having a total of up to 14 carbon atoms; M is a cation with a valence equal to n; and n is an integer with a value of 1 to 5.

2. Curable compositions according to claim 1, wherein said cationically-sensitive monomer is selected from the group consisting of 1,2-, 1,3-, and 1,4-cyclic ethers, vinyl ethers, N-vinyl compounds, ethylenically unsaturated hydrocarbons, cyclic formals, and cyclic organosiloxanes.

3. Curable compositions according to claim 1, wherein said cationically-sensitive monomer comprises epoxide having an epoxy equivalency of from 1 to 6.

4. A process for polymerizing cationically sensitive monomers, comprising the steps of:
(a) mixing with said monomers a catalytically effective amount of acidic cyclic perfluoroaliphaticdisulfonimide or salt thereof comprising a compound of the formula:

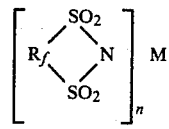

wherein $R_f$ is perfluoroalkylene having 2 to 4 catenary carbon atoms or perfluorocycloalkylene having 4 to 7 ring atoms, $R_f$ optionally being substituted by one or more straight chain, branched, or cyclic perfluoroalkyl groups of 1 to 12 carbon atoms, with $R_f$ having a total of up to 14 carbon atoms, M is a cation with a valence equal to n; and n is an integer with a value of 1 to 5, thereby forming a mixture; and
(b) allowing said mixture to polymerize, or heating said mixture to effect polymerization thereof.

5. A process according to claim 4, wherein said cationically-sensitive monomer comprises epoxide having an epoxy equivalency of from 1 to 6.

* * * * *